US00PP36611P2

(12) United States Plant Patent
Koning

(10) Patent No.: US PP36,611 P2
(45) Date of Patent: Apr. 15, 2025

(54) ***LAVANDULA* PLANT NAMED 'Anouk Deluxe 201908'**

(50) Latin Name: *Lavandula stoechas*
Varietal Denomination: Anouk Deluxe 201908

(71) Applicant: L. KONING BEHEER B.V., Nuis (NL)

(72) Inventor: Lammert Koning, Nuis (NL)

(73) Assignee: L. KONING BEHEER B.V., Nuis (NL)

( * ) Notice: Subject to any disclaimer, the term of this patent is extended or adjusted under 35 U.S.C. 154(b) by 0 days.

(21) Appl. No.: 18/787,346

(22) Filed: Jul. 29, 2024

(51) Int. Cl.
*A01H 5/02* (2018.01)
*A01H 6/50* (2018.01)

(52) U.S. Cl.
USPC ..... Plt./445
CPC ..... *A01H 6/502* (2018.05)

(58) Field of Classification Search
USPC ..... Plt./445
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Lavandula* plant named 'Anouk Deluxe 201908', characterized by its compact, broadly upright and uniformly mounded plant habit; freely branching growth habit; dense and bushy appearance; freely flowering habit; dark purple-colored flowers with showy lighter purple-colored terminal flower bracts positioned on short, strong and erect peduncles; and good garden performance.

2 Drawing Sheets

Figure 1:
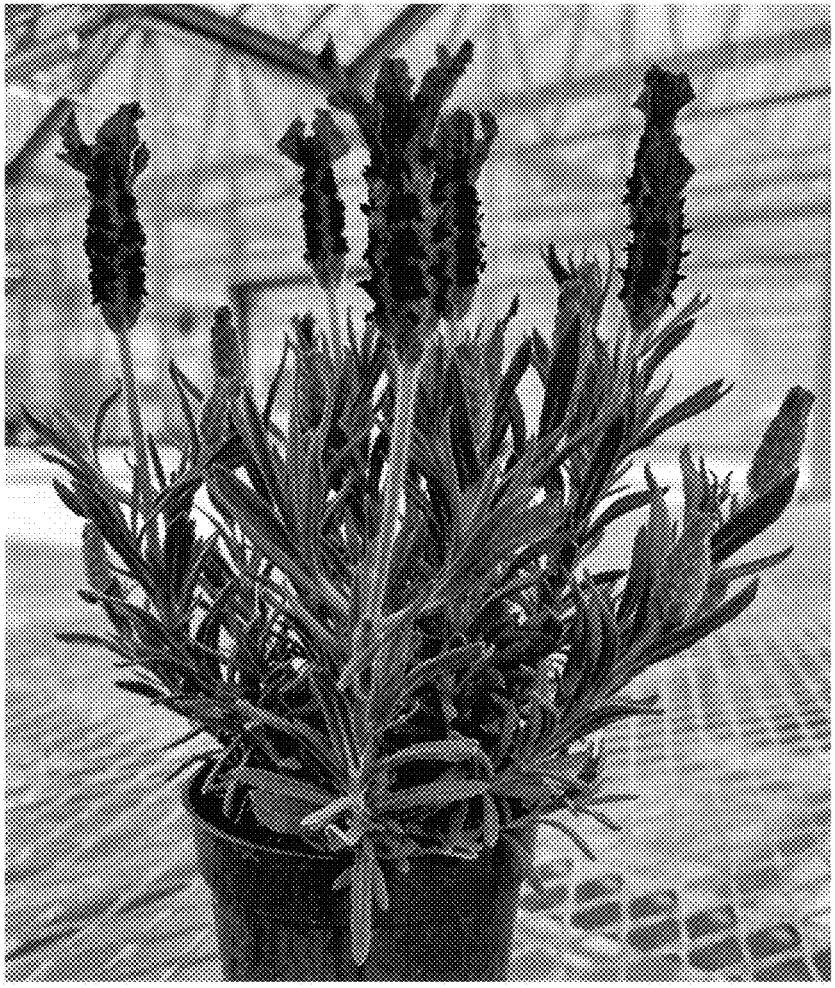

Botanical designation: *Lavandula stoechas.*
Cultivar denomination: 'ANOUK DELUXE 201908'.

BACKGROUND OF THE INVENTION

The present invention relates to a new and distinct *Lavandula* plant, botanically known as *Lavandula stoechas*, commonly referred to as Lavender and hereinafter referred to by the name 'Anouk Deluxe 201908'.

The new *Lavandula* plant is a product of a planned breeding program conducted by the Inventor in Boskoop, The Netherlands. The objective of the breeding program was to develop new unique *Lavandula* plants with good performance and attractive plant form and flower coloration.

The new *Lavandula* plant originated from an open-pollination in June 2018 of a proprietary selection of *Lavandula stoechas* identified as code number LK201707, not patented, as the female, or seed, parent with an unknown proprietary selection of *Lavandula stoechas* as the male, or pollen, parent. The new *Lavandula* plant was discovered and selected by the Inventor as a single flowering plant within the progeny of the stated open-pollination in a controlled environment in Boskoop, The Netherlands in June 2019.

Asexual reproduction of the new *Lavandula* plant by terminal cuttings in a controlled greenhouse environment in Boskoop, The Netherlands since September 2019 has shown that the unique features of this new *Lavandula* plant are stable and reproduced true to type in successive generations.

SUMMARY OF THE INVENTION

Plants of the new *Lavandula* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of the new *Lavandula* plant. These characteristics in combination distinguish 'Anouk Deluxe 201908' as a new and distinct *Lavandula* plant:

1. Compact, broadly upright and uniformly mounded plant habit.
2. Freely branching growth habit; dense and bushy appearance.
3. Freely flowering habit.
4. Dark purple-colored flowers with showy lighter purple-colored terminal flower bracts positioned on short, strong and erect peduncles.
5. Good garden performance.

Plants of the new *Lavandula* differ primarily from plants of the female parent selection in the following characteristics:

1. Flowers of plants of the new *Lavandula* have more terminal flower bracts than flowers of plants of the female parent selection.
2. Terminal flower bracts of plants of the new *Lavandula* are larger than terminal flower bracts of plants of the female parent selection.

Plants of the new *Lavandula* can be compared to plants of the *Lavandula stoechas* 'Anouk Deluxe 1205', disclosed in U.S. Plant Pat. No. 28,264. In side-by-side comparisons, plants of the new *Lavandula* differ primarily from plants of 'Anouk Deluxe 1205' in the following characteristics:

1. Plants of the new *Lavandula* are broader than and not as upright as plants of 'Anouk Deluxe 1205'.
2. Leaves of plants of the new *Lavandula* are broader than leaves of plants of 'Anouk Deluxe 1205'.

3. Plants of the new *Lavandula* have lighter colored terminal flower bracts than plants of 'Anouk Deluxe 1205'.

Plants of the new *Lavandula* can also be compared to plants of the *Lavandula stoechas* 'Anouk', disclosed in U.S. Plant Pat. No. 16,685. In side-by-side comparisons, plants of the new *Lavandula* differ primarily from plants of 'Anouk' in the following characteristics:

1. Plants of the new *Lavandula* are broader than and not as upright as plants of 'Anouk'.
2. Leaves of plants of the new *Lavandula* are broader than leaves of plants of 'Anouk'.
3. Flowers of plants of the new *Lavandula* have more terminal flower bracts than flowers of plants of 'Anouk'.
4. Plants of the new *Lavandula* have darker colored terminal flower bracts than plants of 'Anouk'.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet (FIG. 1) is a side perspective view of a typical flowering plant of 'Anouk Deluxe 201908' grown in a container.

Figure 2:
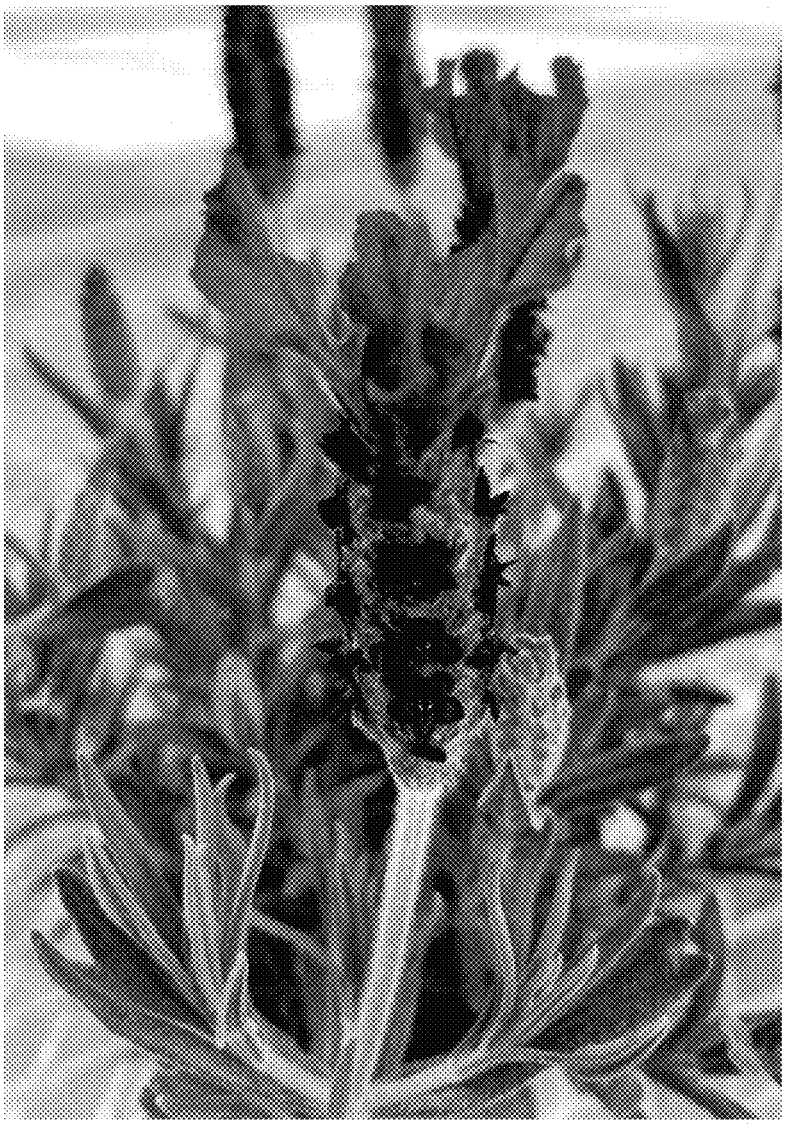

The photograph on the second sheet (FIG. 2) is a close-up view of a typical flowering plant of 'Anouk Deluxe 201908'.

DETAILED BOTANICAL DESCRIPTION

Plants used in the aforementioned photographs and following detailed description were grown in 10.5-cm containers during the winter and early spring in a glass-covered greenhouse in Elburn, Illinois and under cultural practices typical of commercial *Lavandula* production. Plants were six months old when the photographs and description were taken. During the production of the plants, day temperatures ranged from 7.8° C. to 18.2° C. and night temperatures ranged from 6.3° C. to 14.5° C. In the following description, color references are made to The Royal Horticultural Society Colour Chart, 2015 Edition, except where general terms of ordinary dictionary significance are used.

Botanical classification: *Lavandula stoechas* 'Anouk Deluxe 201908'.

Parentage:

*Female, or seed, parent*.—Proprietary selection of *Lavandula stoechas* identified as code number LK201707, not patented.

*Male, or pollen, parent*.—Unknown proprietary selection of *Lavandula stoechas*, not patented.

Propagation:

*Type*.—Terminal vegetative cuttings.

*Time to initiate roots, summer and winter*.—About ten days at temperatures about 18° C.

*Time to produce a rooted young plant, summer*.—About 60 days at temperatures about 20° C.

*Time to produce a rooted young plant, winter*.—About 70 days at temperatures about 20° C.

*Root description*.—Fine, fibrous; initially white in color and becoming more brown with development; actual color of the roots is dependent on substrate composition, water quality, fertilizer type and formulation.

*Rooting habit*.—Freely branching; dense.

Plant description:

*Plant and growth habit*.—Herbaceous perennial; compact, broadly upright and uniformly mounding plant habit; obovate in overall plant shape; freely branching habit; moderately vigorous growth habit and moderate growth rate; flowers arranged in verticillasters on crowded spikes with showy terminal flower bracts.

*Plant height, soil level to top of foliar plane*.—About 14 cm to 15 cm.

*Plant height, soil level to top of floral plane*.—About 17 cm to 19 cm.

*Plant width*.—About 20 cm to 24 cm.

*Lateral branch description*.—Quantity per plant: About 18 to 22 primary lateral branches each with potentially two secondary lateral branches developing at every node; pinching will enhance branching potential. Length: About 14 cm to 15 cm. Diameter: About 2 mm to 2.5 mm. Internode length: About 1.2 cm to 1.4 cm. Strength: Moderately strong; flexible. Aspect: Mostly upright to slightly outwardly. Texture and luster: Densely tomentose; slightly glossy. Color, when developing: Close to 144A to 144B. Color, developed: Close to 144B to 144C; if woody, close to 200A to 200B.

*Leaf description*.—Arrangement: Opposite, simple; sessile. Length: About 3.3 cm to 3.5 cm. Width: About 6 mm to 7 mm. Shape: Linear. Apex: Acute to acuminate. Base: Cuneate. Margin: Entire; slightly to moderately revolute; not lobed. Texture and luster, upper and lower surfaces: Densely tomentose; matte. Fragrance: Strongly aromatic, pungent. Venation pattern: Pinnate. Color: Developing leaves, upper surface: Close to between 144A and 146A. Developing leaves, lower surface: Close to 146B. Fully expanded leaves, upper surface: Close to NN137B to NN137C; venation, close to 146B. Fully expanded leaves, lower surface: Close to 137B; venation, close to 138A to 138B.

Flower description:

*Flower type, arrangement and habit*.—Small single salverform flowers arranged in compact verticillasters on crowded terminal spikes; freely flowering, about 90 to 104 flowers developing per inflorescence; flowers with two-lobed upper lip and three-lobed lower lip; flowers face mostly outwardly on the spike; inflorescences with showy terminal flower bracts.

*Natural flowering season*.—Long flowering period; continuous from late spring into the summer in The Netherlands; plants reblooming.

*Flower longevity on the plant*.—Individual flowers last about eight to twelve weeks on the plant depending on environmental conditions; flowers not persistent.

*Fragrance*.—None detected.

*Flower buds*.—Length: About 1 cm. Diameter: About 5 mm. Shape: Conical. Texture and luster: Densely tomentose; matte. Color: Close to 144A to 144B.

*Inflorescence size*.—Height, excluding terminal flower bracts: About 3 cm to 3.3 cm. Diameter, excluding t terminal flower bracts: About 1 cm to 1.2 cm.

*Flower size*.—Diameter: About 5 mm. Depth (height): About 9 mm. Throat diameter: About 1.25 mm. Tube length: About 6 mm. Tube diameter: About 1 mm.

*Petals*.—Quantity and arrangement: Upper lip, two-lobed and lower lip, three-lobed. Length, upper and lower lips: About 2 mm to 2.5 mm. Width, upper and lower lips: About 2 mm. Shape, upper lip: Obovate. Shape, lower lip: Ovate. Apex, upper and lower lips: Acute. Margin, upper and lower lips: Entire; slightly undulate. Texture and luster, upper and lower lips, upper surface: Smooth, glabrous; slightly velvety; matte. Texture and luster, upper and lower lips, lower surface: Smooth, glabrous; slightly velvety; slightly glossy. Color, upper and lower lips: When opening and fully opened, upper surface: Close to 83A. When opening and fully opened, lower surface: Close to 83B. Throat: Distally, close to 83A and proximally, close to 85A to 85B. Tube: Close to 85A to 85B.

*Basal flower bracts*.—Quantity and arrangement: Each group of four to six flowers is subtended by a single basal flower bract. Length: About 1 cm. Width: About 6 mm to 7 mm. Shape: Spatulate to rhomboidal. Apex: Acuminate. Base: Truncate. Margin: Entire. Texture and luster, upper and lower surfaces: Smooth, glabrous; margins, pubescent; slightly glossy. Color, upper surface: Translucent, close to NN155D with venation, close to 143A. Color, lower surface: Close to 145D; venation, close to 144A.

*Terminal flower bracts*.—Quantity and arrangement: About 12 to 16 positioned mostly upright at inflorescence apex. Length: About 2.5 cm. Width: About 1.4 cm to 1.8 cm. Shape: Obovate; undulate and ruffled appearance. Apex: Acute to acuminate. Base: Cuneate. Margin: Entire; undulate, ruffled. Texture and luster, upper and lower surfaces: Smooth, glabrous; matte. Color, upper surface: Close to N82A; venation, close to 143A. Color, lower surface: Close to N82A to N82B; venation, close to 146A.

*Sepals*.—Quantity and arrangement: Five, fused into a campanulate tube. Calyx length: About 9 mm. Calyx diameter: About 2.5 mm to 3 mm. Shape: Lanceolate. Apex: Obtuse. Margin: Entire. Texture and luster, upper (inner) and lower (outer) surfaces: Densely pubescent; matte. Color: When opening and fully opened, upper surface: Close to between 143A and 144A. When opening and fully opened, lower surface: Distally, close to 143A and proximally, close to 144B.

*Peduncles*.—Length: About 2.5 cm to 3.2 cm. Diameter: About 2 mm to 2.5 mm. Aspect: Mostly upright. Strength: Strong; flexible. Texture and luster: Densely tomentose; matte. Color: Close to between 143A and 144A.

*Reproductive organs*.—Stamens: Quantity per flower: Four. Filament length: About 1 mm. Filament color: Close to N155A. Anther shape: Reniform to short oblong; dorsifixed. Anther size: About 0.75 mm by 0.75 mm. Anther color: Close to 12A. Pollen amount: None observed. Pistils: Quantity per flower: One. Pistil length: About 3 mm. Stigma shape: Club-shaped. Stigma diameter: About 0.5 mm. Stigma color: Close to N79A. Style length: About 2.25 mm. Style color: Close to 157D. Ovary color: Close to 143A to 143B.

*Seeds and fruits*.—To date, seed and fruit production has not been observed on plants of the new *Lavandula*.

Pathogen & pest resistance: To date, plants of the new *Lavandula* have not been noted to be resistant to pathogens and pests common to *Lavandula* plants.

Garden performance: Plants of the new *Lavandula* have exhibited good tolerance to rain and wind and have been observed to tolerate temperatures from about 1° C. to about 35° C.

It is claimed:

1. A new and distinct *Lavandula* plant named 'Anouk Deluxe 201908' as herein illustrated and described.

* * * * *